(12) United States Patent
Klemmensen et al.

(10) Patent No.: US 6,215,023 B1
(45) Date of Patent: Apr. 10, 2001

(54) PROCESS FOR THE PREPARATION OF CYCLOPROPANE CARBOXYLIC ACIDS

(75) Inventors: Per Dausell Klemmensen; Hans Kolind-Andersen; Ib Winckelmann, all of Lemvig (DK)

(73) Assignee: Cheminova Agro A/S, Harboør (DK)

( * ) Notice: Subject to any disclaimer, the term of this patent is extended or adjusted under 35 U.S.C. 154(b) by 0 days.

(21) Appl. No.: 09/622,444

(22) PCT Filed: Feb. 15, 1999

(86) PCT No.: PCT/DK99/00067

§ 371 Date: Aug. 17, 2000

§ 102(e) Date: Aug. 17, 2000

(87) PCT Pub. No.: WO99/42432

PCT Pub. Date: Aug. 26, 1999

(30) Foreign Application Priority Data

Feb. 18, 1998 (DK) .................................................. 023098

(51) Int. Cl.⁷ .......................... C07C 61/04; C07C 61/16

(52) U.S. Cl. ............................................ 562/506; 562/510

(58) Field of Search ...................................... 562/506, 510

(56) References Cited

U.S. PATENT DOCUMENTS 5,986,130 * 11/1999 Klemmensen et al. ............. 562/506

* cited by examiner

*Primary Examiner*—Joseph K. McKane
*Assistant Examiner*—Joseph Murray
(74) *Attorney, Agent, or Firm*—Browdy and Neimark

(57) ABSTRACT

Preparation of cyclopropane carboxylic acids usable as intermediates and of formula (II), wherein $R_1$ represents halogen, preferably Cl or Br, or haloalkyl, preferably $CF_3$, and $X_2$ represents halogen, preferably Cl or Br, where $R_1$ or $X_2$ may be the same or different, and wherein the configuration of (II) is predominantly Z for $R_1=CF_3$ and $X_2=Cl$; by reacting, in the presence of a catalyst, a compound of formula (I), wherein $R_1$ and $X_2$ are as defined, and $X_1$ represents halogen, preferably Cl or Br, where $R_1$, $X_1$ and $X_2$ may be the same or different, with a compound which is a hydrogen donor.

18 Claims, No Drawings

PROCESS FOR THE PREPARATION OF CYCLOPROPANE CARBOXYLIC ACIDS

CROSS REFERENCE TO RELATED APPLICATION

The present application is the national stage under 35 U.S.C. 371 of PCT/DK99/00067, filed Feb. 15, 1999.

The present invention relates to processes for the preparation of compounds usable as intermediates in the preparation of cyclopropane carboxylic esters.

Cyclopropane carboxylic esters are insecticidally active compounds which are known as "pyrethroids", and since they combine exceptionally good insecticidal properties with very low toxicity to mammals they are of considerable interest. Therefore, much effort has been made in order to find economically favourable routes for preparing them and their most important intermediates.

A selection of these pyrethroid compounds showing a remarkably high activity can be prepared from acids of the general formula II, where the carbon atoms marked 1 and 3 are asymmetrical carbon atoms and where the geometry in the cyclopropane ring is 1R,cis, i.e., the absolute configuration at carbon atom 1 is R and the two hydrogen atoms at carbon atoms 1 and 3 are in cis-position. The compounds II can be prepared from the compounds I. $R_1$ represents a halogen atom (e.g., Cl or Br) or haloalkyl (e.g., $CF_3$). $X_1$ and $X_2$ represents halogen atoms (e.g., Cl or Br). $R_1$, $X_1$ and $X_2$ may be the same or different.

Scheme 1

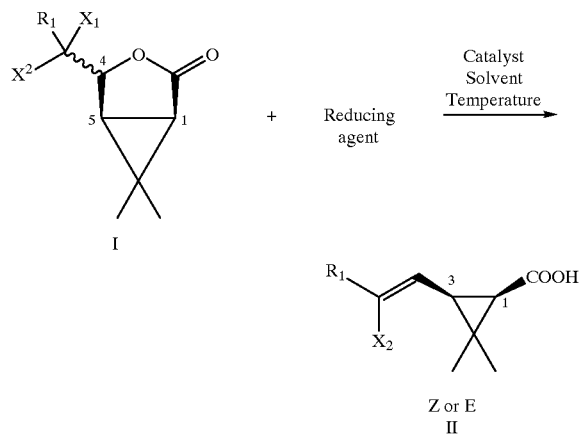

The superscripts [1,2 etc.] in the following description refer to the list of references stated at the end of the present description.

It is known[1,2,3] that the acid II should have the geometry 1R,cis in order that pyrethroids derived therefrom can obtain maximum insecticidal activity. If $R_1$ and $X_2$ are $CF_3$ and Cl, respectively, it is further more known that the chlorine atom and cyclopropane group should be at the same side of the carbon-carbon double bond, Z configuration, in order to obtain maximum insecticidal activity, which is shown in Scheme 1.

Therefore, it is of great importance to be able to prepare the exact isomer of II which provides the most active pyrethroids in a technically as well as economically attractive manner in order to minimize in this way the applied amount of active substance (insecticide) in the treatment of agricultural crops, habitations and the like.

The preparation of II of the desired 1R,cis configuration takes place from the intermediate I where the configuration is already present. In addition to the asymmetric centres at positions 1 and 5, the intermediate I has an asymmetric carbon atom at position 4, which means that I can occur in the two configurations 1R,4R,5S and 1R,4S,5S where, however, the synthesis of I preferably leads to 1R,4R,5S. In the further reaction of I both configurations lead to II.

The desired configuration of I at carbon atoms 1 and 5 is obtained through known synthetic steps from the natural product Δ-3-carene[4,5,6,7] which in the terminology of chiral chemistry is said to belong to "the chiral pool", i.e. the collection of relatively inexpensive and readily available natural substances of a described configuration among which one can find starting materials of a particular, desired configuration.

It is known[6,7] that the reduction I→II can be carried out by metallic zinc or other metals (e.g., magnesium). Reactions corresponding to the transformation I→II are called "elimination of β-halo esters" and can be carried out under different conditions[10]. A comprehensive review work[10] discusses several possible sets of conditions for carrying out such reactions, inter alia, reaction with Zn and electrolysis. Reactants equal or analogous to those used in the present invention are not mentioned.

Apparently, previously described[8] trans-β-bromo-acetoxy elimination reactions are only practicable on systems wherein bromine is further activated by an ester group, since experiments under the conditions described ($NaHSO_3$, $Na_2SO_3$) gave, for the starting compound I ($R_1=X_1=X_2=Br$), only a little II ($R_1=X_2=Br$) and more III ($R_2=X_2=Br$) (see Scheme 2) together with unreacted starting compound. Experiments under the conditions described ($NaHSO_3$, $NaHCO_3$) gave no reaction for I ($R_1=CF_3$; $X_1=X_2=Cl$), not even in the presence of a catalyst (Pt).

However, it has unexpectedly been found that just the halolactone I in the presence of metal catalysts (e.g., Pt, Pd, Ni, Rh, or Os) can be reduced to the cyclopropane carboxylic acid II by using formate ($HCOO^-$), hypophosphite ($H_2PO_2^-$), phosphite ($HPO_3^{2-}$) or hydrogen ($H_2$), respectively, as reducing agent.

Simultaneously, it has unexpectedly been found that if $R_1=CF_3$ and $X_1=X_2=Cl$, the product II consists predominantly of the desired Z-isomer.

This synthetic route is totally specific in respect of the stereoisomerism of the products so that the geometry of I can be found again in the product II. In this way costly racemate resolutions as well as yield losses to useless isomers are avoided.

Previous attempts[9] to reduce similar halolactone systems with hydrogen in the presence of a metal catalyst [Pd(C)5%] resulted in simple dehalogenation only, with the lactone ring being maintained.

Here is described a number of new synthetic methods for the preparation of the (1R,cis)-acid moiety of the pyrethroid esters of formula II from the halolactone I. These synthetic methods can be used in the same way to prepare the racemic (1RS,cis)-acid moiety of the pyrethroid esters from racemic halolactones which in turn are synthesized from racemic Biocartol.

In accordance with the above the invention relates to a process for the preparation of cyclopropane carboxylic acids of the general formula II, wherein the substituent $R_1$ represents a halogen atom, preferably Cl or Br, or haloalkyl (halo in haloalkyl being, e.g., fluoro, chloro or bromo, and alkyl in haloalkyl being suitably a lower alkyl such as alkyl having 1–3 carbon atoms), preferably $CF_3$, and the substituent $X_2$ represents a halogen atom, preferably Cl or Br, where $R_1$ and $X_2$ may be the same or different, and wherein the configuration of II predominantly is Z for $R_1=CF_3$ and $X_2=Cl$, which process is characterized by reacting, in the presence of a catalyst, a compound of the general formula I, wherein the substituents $R_1$ and $X_2$ are as defined above, and the substituent $X_1$ represents a halogen atom, preferably Cl or Br, where $R_1$, $X_1$ and $X_2$ may be the same or different, with a compound which is a hydrogen donor.

A great advantage of the present invention is that the use of expensive reducing agents such as Zn or other metals can be avoided and that, e.g., hydrogen can be used instead.

A further advantage of the present invention is that, as by-products, carbon dioxide ($CO_2$)+sodium chloride (NaCl), phosphorous acid ($H_3PO_3$)+sodium chloride (NaCl), phosphoric acid ($H_3PO_4$)+sodium chloride (NaCl) or hydrochloric acid (HCl), respectively, are obtained instead of zinc ions or other metal ions.

Zinc is an element for which maximum concentrations have been set, if it is to be discharged with wastewater or spread with sludge from a purification plant. This means that a production using zinc in major amounts will have to incorporate an expenditure demanding step for recovering the applied zinc. The same conditions apply to other metals.

Use can be made of various appropriate embodiments of the process of the invention as stated in claims 2–7.

The process of the invention and its various embodiments are caracteristic by being ideal and not previously described for the preparation of II from I.

By suitably selecting solvent, temperature, calatyst and pH level in the reaction mixture, it is possible to minimize the occurrence of undesirable by-products of the general formulae III, IV and/or V:

Scheme 2

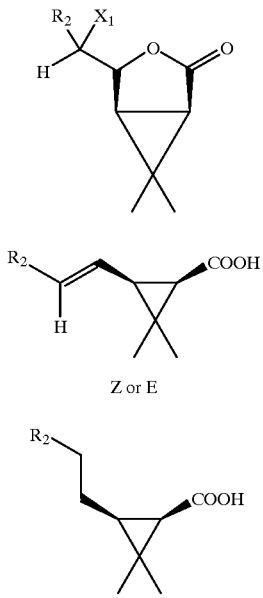

$R_2$ represents hydrogen (H), a halogen atom (e.g., Cl or Br) or haloalkyl (e.g., $CF_3$). $X_1$ represents a halogen atom (e.g., Cl or Br). $R_2$ and $X_1$ may be the same or different.

By selecting solvent, temperature, catalyst and pH level in the reaction mixture it is likewise possible to control the reaction to preferably give the desired Z- or E-isomer of II.

NMR and HPLC analyses of the end product II ($R_1=CF_3$; $X_2=Cl$) show that there is preferably isolated Z-isomer, usually more than 95% of Z-isomer, and the crude product is easily purified to be more than 99% of Z-isomer. However, in most cases it holds that a content >95% of Z-isomer is satisfactory. A costly further purification can therefore be avoided, which is not the case when II ($R_1=CF_3$; $X_2=Cl$) is prepared via the conventional metal reduction.

In the reduction of I to II use can be made of formate (in the form of a metal salt, ammonium salt or other salts), hypophosphite (in the form af a metal salt, ammonium salt or other salts) and phosphite (in the form of a metal salt, ammonium salt or other salts). These three agents are often used in the reactions named "transfer hydrogenation". In the reduction of I to II gaseous hydrogen can alternatively be used. If hydrogen is used as reducing agent, the reaction can be carried out at atmospheric pressure as well as at elevated pressure, e.g., confined in an autoclave.

The reduction reaction is carried out in a solvent or in mixtures of solvents, the properties of which can vary much. Both protic and aprotic solvents are used, and among the usable aprotic solvents both polar and nonpolar ones exist. Suitable as a solvent for reactions with formate, hypophosphite and phosphite are alcohols (e.g., methanol and ethylene glycol) with more or less water or DMF admixed therewith. Suitable as a solvent for reactions with hydrogen are alcohols (e.g., methanol and 2-methoxyethanol) and aprotic, polar solvents (e.g., DMF, DMSO and acetonitrile) with more or less water admixed therewith. The concentration of the reaction components in the solvent or solvent mixture may be in the range of 1–80% and is typically in the range of 10–30%.

The reduction reaction is carried out in the presence of a metal catalyst. Suitable as a catalyst are transition metals, e.g., Pt, Pd, Ni, Rh and Os. The catalyst can be finely divided as small particles or finely divided on activated carbon or other inert carrier materials.

The reduction reaction is carried out within a wide pH range, but advantageously in an alkaline medium which is obtained by adding to the reaction mixture pH adjusting compounds (e.g., NaOH, ammonia, amines, $NaHCO_3$, $Na_2CO_3$, $NaH_2PO_4$, and $Na_2HPO_4$). The pH adjustment can be carried out by a pH-meter provided with a titrator, the reservoir of which has been provided with aqueous solutions of said pH adjusting compounds.

The reduction reaction is carried out in a wide temperature range and not unexpected the reaction proceeds faster at higher temperature. Within the range 0–100° C., preferably 20–70° C., a reasonable reaction rate is obtained. In the conversion of I ($R_1=CF_3$; $X_1=X_2=Cl$) into II ($R_1=CF_3$; $X_2=Cl$) it is of importance to obtain a high content of the Z-isomer. It has been found that lower temperature promotes the content of the Z-isomer (at, e.g., 20° C. there is obtained Z/E>30).

By the embodiments of the process of the invention as stated in claims 8 to 10, from the following compounds of formula I:

(1R,4R,5S)-4-(1,1-dichloro-2,2,2-trifluoroethyl)-6,6-dimethyl-3-oxabicyclo[3.1.0]hexan-2-one, (1R,4R(or 4S),5S)-6,6-dimethyl-4-(trichloromethyl)-3-oxabicyclo[3.1.0]hexan-2-one and (1R,4R(or 4S),5S)-6,6-dimethyl-4-(tribromomethyl)-3-oxabicyclo [3.1.0]hexan-2-one there are obtained the following compounds of formula II:

Z-(1R-cis)-3-(2-chloro-3,3,3-trifluoro-1-propenyl)-2,2-dimethyl-cyclopropane carboxylic acid, (1R-cis)-3-(2,2-dichloroethenyl)-2,2-dimethyl-cyclopropane carboxylic acid and (1R-cis)-3-(2,2-dibromoethenyl)-2,2-dimethyl-cyclopropane carboxylic acid.

The invention is further illustrated in the following examples. Yields and purities were determined by gas and/or liquid chromatography, as well as NMR spectroscopy. Identification was effected by means of NMR spectroscopy and GC/MS.

EXAMPLE 1

(1R-cis)-3-(2,2-Dibromoethenyl)-2,2-dimethyl-cyclopropane carboxylic acid (II, $R_1=X_2=Br$).

A mixture of (1R,4R,5S)-6,6-dimethyl-4-(tribromomethyl)-3-oxabicyclo[3.1.0]hexan-2-one (I, $R_1=X_1=X_2=Br$) and (1R,4S,5S)-6,6-dimethyl-4-(tribromomethyl)-3-oxabicyclo[3.1.0]hexan-2-one (I, $R_1=X_1=X_2=Br$), 0.38 g (0.001 mol), is stirred with sodium hydrogen carbonate, 0.126 g (0.0015 mol), sodium formate, 0.27 g (0.004 mol), and Pt(C) 5%, 0.03 g, in about 4 ml of methanol at 50° C. for 5.5 hours. The reaction mixture is acidified with aqueous hydrochloric acid and extracted twice with methyl t-butyl ether which is dried and evaporated. There is obtained 0.28 g of purity 61% (GC, area-%). The retention time is identical to that of II prepared according to Ref.[6], and MS (Mass (intensity in % of base peak): 296 (5) $M^+$, 298 (9) $(M+2)^+$, 300 (4) $(M+4)^+$, 255 (24), 253 (45), 251 (23), 219 (100), 217 (98), 201 (18), 199 (22), 197 (13), 174 (29), 172 (33)) is identical to MS of II prepared according to Ref.[6].

EXAMPLE 2

(1R-cis)-3-(2,2-Dibromoethenyl)-2,2-dimethyl-cyclopropane carboxylic acid (II, $R_1=X_2=Br$).

A mixture of (1R,4R,5S)-6,6-dimethyl-4-(tribromomethyl)-3-oxabicyclo [3.1.0]hexan-2-one (I, $R_1=X_1=X_2=Br$) and (1R,4S,5S)-6,6-dimethyl-4-(tribromomethyl)-3-oxabicyclo[3.1.0]hexan-2-one (I, $R_1X_1=X_2=Br$), 0.75 g (0.002 mol), is stirred with sodium hydrogen carbonate, 0.421 g (0.005 mol), and-Pt(C) 5%, 0.06 g in about 9 ml of methanol at 50° C. with gaseous hydrogen being supplied below the liquid surface. Samples taken out for GC analysis are treated with aqueous hydrochloric acid/methyl t-butyl ether and analysed on GC. Already after 1 hour GC analysis (area-%) shows a content of 42% of II and 34% of unreacted I. Identification of II is effected as shown in Example 1.

EXAMPLE 3

(1R-cis)-3-(2,2-Dichioroethenyl)-2,2-dimethyl-cyclopropane carboxylic acid (II, $R_1=X_2=Cl$).

A mixture of (1R,4R,5S)-6,6-dimethyl-4-(trichloromethyl)-3-oxabicyclo[3.1.0]hexan-2-one (I, $R_1=X_1=X_2=Cl$) and (1R,4S,5S)-6,6-dimethyl-4-(trichloromethyl)-3-oxabicyclo[3.1.0]hexan-2-one (I, $R_1=X_1=X_2=Cl$), 0.24 g (0.001 mol), is stirred with sodium hydrogen carbonate, 0.21 g (0.0025 mol), and Pd(C) 5%, 0.01 g, in about 4 ml of DMF at 50° C. under a hydrogen atmosphere of a slight overpressure. After stirring for ½ hour at 50° C. the mixture is stirred at room temperature. Samples taken out for GC analysis are treated with aqueous hydrochloric acid/methyl t-butyl ether and analysed on GC. After 16 hours GC analysis (area-%) shows a content of 39% of II and 32% of unreacted I. The retention time is identical to that of II prepared according to Ref.[6], and MS (Mass (intensity in % of base peak): 208 (6) M+, 210 (4) (M+2)+, 175 (25), 173 (78), 165 (27), 163 (39), 111 (22), 109 (28), 91 (100), 77 (46), 39 (64)) is identical to MS of II prepared according to Ref.[6].

EXAMPLE 4

(1R-cis)-3-(2, 2-Dichloroethenyl)-2, 2-dimethyl-cyclopropane carboxylic acid (II, $R_1X_2=Cl$).

(1R,4R,5S)-6,6-Dimethyl-4-(trichloromethyl)-3-oxabicyclo[3.1.0]hexan-2-one (I, $R_1=X_1=X_2=Cl$), 0.24 g (0.001 mol), is stirred with sodium hydrogen carbonate, 0.17 g (0.002 mol), sodium formate, 0.34 g (0.005 mol) and Pd(C) 5%, about 0.03 g in about 6 ml of methanol at 50° C.

Samples taken out for GC analysis are treated with aqueous hydrochlorid acid/methyl t-butyl ether and analysed on GC. After 6 hours GC analysis (area-%) shows a content of 68% of II and 16% of unreacted I. Identification of II is effected as shown in Example 3.

EXAMPLE 5

Z-(1R-cis)-3-(2-chloro-3,3,3-trifluoro-1-propenyl)-2,2-dimethyl-cyclopropane carboxylic acid (II, $R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 11. 08 g (0.04 mol), is vigorously stirred with sodium carbonate, 6.36 g (0.06 mol), and Pt(C) 5%, 0.4 g, in 80 ml of DMF at 20° C. with an excess of gaseous hydrogen being supplied below the liquid surface.

Samples taken out for GC analysis are treated with aqueous hydrochloric acid/methyl t-butyl ether and analysed on GC. After 4.25 hours GC analysis (area-%) shows a content of 91% of II, 5% of IV (($R_2=CF_3$), 2% of V ($R_2=CF_3$) and 1% of III ($R_2=CF_3$; $X_1$ Cl). The retention time of the present II is identical to that of II prepared as previously described[7].

The reaction mixture is treated with 100 ml of water, freed from catalyst by filtration, acidified (pH≈1) with aqueous hydrochloric acid and extracted twice with methyl t-butyl ether. The ether phase is dried by $Na_2SO_4$ and evaporated to a crystalline mass. HPLC analysis (external standard) shows a yield of 89% of II. HPLC analysis shows Z/E=37.

A recrystallisation from hexane results in pure II containing 1–2% of E-isomer. Further recrystallisation from hexane results in pure II, 100% of Z-isomer. Physical and spectroscopic data of II correspond to those previously described.

EXAMPLE 6

Z-(1R-cis)-3-(2-chloro-3,3,3-trifluoro-1-propenyl)-2,2-dimethyl-cyclopropane carboxylic acid (II, $R_1=CF_3$; $X_2=Cl$).

(1R;4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.28 g (0.001 mol), is stirred with sodium hydrogen carbonate, 0.13 g (0.0015 mol), sodium formate, 0.27 g (0.004 mol), and Pt(C) 5%, about 0.05 g, in about 4 ml of DMF/methanol (2:1) at 50° C.

Samples taken out for GC analysis are treated with aqueous hydrochloric acid/methyl t-butyl ether and analysed on GC. After 7.5 hours GC analysis (area-%) shows complete conversion of I and a content of 90% of II and 7% of III, ($R_2=CF_3$; $X_1=Cl$). HPLC analysis shows for II Z/E=18. Identification of II is effected as shown in Example 5.

EXAMPLE 7

Z-(1R-cis)-3-(2-chloro-3,3,3-trifluoro-1-propenyl)-2,2-dimethyl-cyclopropane carboxylic acid (II, $R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.28 g (0.001 mol), is stirred with ammonium formate, 0.063 g (0.001 mol), and Pd(C) 5%, 0.03 g, in 2.5 ml of methanol at 50° C.

Samples taken out for GC analysis are treated with aqueous hydrochloric acid/methyl t-butyl ether and analysed on GC. After 0.5 hour GC analysis (area-%) shows a content of 29% of II and 71% of unreacted I. Identification of II is effected as shown in Example 5.

EXAMPLE 8
Z-(1R-cis)-3-(2-chloro-3,3,3-trifluoro-1-propenyl)-2,2-dimethyl-cyclopropane carboxylic acid ($R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.28 g (0.001 mol), is stirred with sodium hydrogen carbonate, 0.42 g (0.005 mol), sodium hypophosphite, 0.44 g (0.005 mol), water 0.5 g, and Pd(C) 5%, 0.03 g, in 3 ml of ethylene glycol at 50° C.

Samples taken out for GC analysis are treated with aqueous hydrochloric acid/methyl t-butyl ether and analysed on GC. After 4 hours GC analysis (area-%) shows complete conversion of I and a content of 97% of II and 3% of III ($R_2=CF_3$; $X_1=Cl$). HPLC analysis shows for II Z/E=22. Identification of II is effected as shown in Example 5.

EXAMPLE 9
Z-(1R-cis)-3-(2-chloro-3,3,3-trifluoro-1-propenyl)-2,2-dimethyl-cyclopropane carboxylic acid (II, $R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.55 g (0.002 mol), is stirred with sodium hydrogen carbonate, 0.42 g (0.005 mol), and Pt(C) 5%, 0.06 9, in 10 ml of water af 50° C. with an excess of gaseous hydrogen being supplied below the liquid surface.

Samples taken out for GC analysis are treated with aqueous hydrochloric acid/methyl t-butyl ether and analysed on GC. After 3 hours GC analysis (area-%) shows a content of 63% of II, 5% of V ($R_2=CF_3$) and 31% of unreacted I. Identification of II is effected as shown in Example 5.

EXAMPLE 10
Z-(1R-cis)-3-(2-chloro-3,3,3-trifluoro-1-propenyl)-2,2-dimethyl-cyclopropane carboxylic acid (II, $R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.55 g (0.002 mol), is stirred with sodium hydrogen carbonate, 0.42 g (0.005 mol), and Raney-Ni, 0.2 g in 10 ml of DMF at 50° C. with an excess of gaseous hydrogen being supplied below the liquid surface.

Samples taken out for GC analysis are treated with aqueous hydrochloric acid/methyl t-butyl ether and analysed on GC. After 2 hours GC analysis (area-%) shows complete conversion of I and a content of 98.5% of II and 1.5% of IV ($R_2=CF$) GC analysis (internal standard) shows a yield of 94.5%. HPLC analysis shows for II Z/E=18. Identification of II is effected as shown in Example 5.

EXAMPLE 11
Z-(1R-cis)-3-(2-chloro-3,3,3-trifluoro-1-propenyl)-2,2-dimnethyl-cyclopropane carboxylic acid (II, $R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.55 g (0.002 mol), is stirred with sodium hydrogen carbonate, 0.42 g (0.005 mol), and Rh(C) 5%, 0.06 g, in 10 ml of DMF at 50° C. with an excess of gaseous hydrogen being supplied below the liquid surface.

Samples taken out for GC analysis are treated with aqueous hydrochloric acid/methyl t-butyl ether and analysed on GC. After 1 hour GC analysis (area-%) shows complete conversion of I and a content of 77% of II and 23% of IV ($R_2=CF_3$). HPLC analysis shows for II Z/E=49. Identification of II is effected as shown in Example 5.

EXAMPLE 12
Z-(1R-cis)-3-(2-chloro-3,3,3-trifluoro-7-propenyl)-2,2-dimethyl-cyclopropane carboxylic acid (II, $R_1=CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.55 g (0.002 mol), is stirred with sodium hydrogen carbonate, 0.42 g (0.005 mol), and $OsO_4$ (1% solution in water), 0.08 g, in 10 ml of DMF at 50° C. with an excess of gaseous hydrogen being supplied below the liquid surface.

Samples taken out for GC analysis are treated with aqueous hydrochloric acid/methyl t-butyl ether and analysed on GC. After 5 hours GC analysis (area-%) shows a content of 33% of II, 1% of III ($R_2=CF_3$; $X_1=Cl$) and 66% of unreacted I. Identification of II is effected as shown in Example 5.

EXAMPLE 13
Z-(1R-cis)-3-(2-chloro-3,3,3-trifluoro-1-propenyl)-2,2-dimethyl-cyclopropane carboxylic acid (II, $R_1CF_3$; $X_2=Cl$).

(1R,4R,5S)-4-(1,1-dichloro-2,2,2-trifluoroethyl)-6,6-dimethyl-3-oxabicyclo[3.1.0]hexan-2-one (I, $R_1=CF_3$; $X_1=X_2=Cl$), 0.28 g (0.001 mol)., is stirred with, sodium carbonate, 0.53 g (0.005 mol), sodium phosphite, pentahydrate, 1.08 g (0.005 mol), and Pd(C) 5%, 0.03 g, in 4 ml of ethylene glycol at 50° C.

Samples taken out for GC analysis are treated with aqueous hydrochloric acid/methyl t-butyl ether and analysed on GC. After 3 hours GC analysis (area-%) shows a complete conversion of I and a content of 79% of II and 21% of IV ($R_2=CF_3$). Identification of II is effected as shown in Example 5.

References:
[1] M. Elliott et al., *Pestic. Sci.*, 9, 112–116, (1978)
[2] P. D. Bentley et al., *Pestic. Sci.*, 11, 156–164, (1980)
[3] P. Ackermann et al., *Pestic. Sci.*, 11, 169–179, (1980)
[4] A. K. Mandal et al., *Tetrahedron*, 42, 5715–5728, (1986)
[5] D. Bakshi et al., *Tetrahedron*, 45, 767–774, (1989)
[6] Danish patent application, (Roussel-Uclaf, S.A.) 2849/78 Jun. 26, 1978)
[7] Danish patent (Cheminova Agro A/S) 171797 B1 (Jul. 21, 1995)
[8] J. A. J. M. Vekemans et al., *J. Org. Chem.*, 53, 627–633, (1988)
[9] J. Goldman et al., *Acta Chem. Scand.*, B28, 492–500, (1974)
[10] Richard C. Larock, *Comprehensive Organic Transformations: A Guide to Functional Group Preparations*, VCH Publishers Inc. 1989, 138–139

What is claimed is:
1. A process for the preparation of cyclopropane carboxylic acids of the general formula II

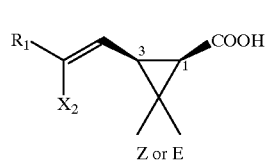

wherein the substituent $R_1$ represents a halogen atom or haloalkyl, and the substituent $X_2$ represents a halogen atom, where $R_1$ and $X_2$ may be the same or different, and wherein the configuration of II is Z for $R_1=CF_3$ and $X_2=Cl$, characterized by reacting, in the presence of a catalyst, a compound of the general formula I

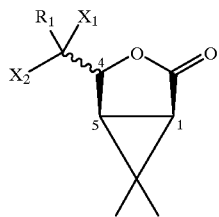

wherein the substituents $R_1$ and $X_2$ are as defined above, and
the substituent $X_1$ represents a halogen atom, where $R_1$, $X_1$ and $X_2$ may be the same or different,
with a compound which is a hydrogen donor.

2. A process according to claim 1, wherein, as a hydrogen donor, use is made of a compound which is known as being a "transfer hydrogenation" agent.

3. A process according to claim 1, wherein, as a hydrogen donor, it is made of gaseous hydrogen, ($H_2(g)$).

4. A process according to claim 2, wherein the catalyst present during the reduction reaction is a transition metal.

5. A process according to claim 1, wherein the reduction reaction is carried out in a solvent or a mixture of solvents.

6. A process according to claim 5, wherein the reduction reaction is carried out in the presence of a pH adjusting compound or a mixture of pH adjusting compounds.

7. A process according to claim 6, wherein the reduction reaction is carried out at a temperature being above the solidification point of the reaction mixture and being at or below the boiling point of the solvent or the solvent mixture under the given apparatus conditions.

8. A process claim 1, wherein the compound prepared from compound I,
wherein the substituent $R_1$ represents $CF_3$, and
the substituents $X_1$ and $X_2$ each represents Cl,
is compound II,
wherein the substituent $R_1$ represents $CF_3$, and
the substituent $X_2$ represents Cl, and
wherein the configuration is Z.

9. A process according to claim 1, wherein the compound prepared from compound I,
wherein the substituents $R_1$, $X_1$ and $X_2$ each represents Cl,
is compound II,
wherein the substituents $R_1$ and $X_2$ each represents Cl.

10. A process according to claims 1, wherein the compound prepared from compound I,
wherein the substituents $R_1$, $X_1$ and $X_2$ each represents Br,
is compound II,
wherein the substituents $R_1$ and $X_2$ each represents Br.

11. The process according to claim 1 wherein $R_1$ is selected from the group consisting of Cl, Br, and $CF_3$.

12. The process according to claim 1 wherein $X_2$ is selected from the group consisting or Cl and Br.

13. The process according to claim 1 wherein $X_1$ is selected from the group consisting of Cl and Br.

14. The process according to claim 4 wherein the transition metal is selected from the group consisting of Pt, Pd, In, Rh and Os.

15. The process according to claim 5 wherein the solvents are selected from the group consisting of alcohols, DMF, DMSO, acetonitrile, and water.

16. The process according to claim 6 wherein the pH adjusting compound is selected from the group consisting of alkali metal hydroxides, ammonia, amines, alkali metal carbonates, alkali metal hydrogen carbonates, alkali metal monohydrogen phosphates, alkali metal dihydrogen phosphates, and mixture thereof.

17. The process according to claim 7 wherein the temperature is between 20 and 70° C.

18. The process according to claim 2, wherein the transfer hydrogenation agent is selected from the group consisting of formates, hypophosphates and phosphates.

* * * * *